US005288869A

United States Patent [19]

Giroldini et al.

[11] Patent Number: 5,288,869

[45] Date of Patent: Feb. 22, 1994

[54] PENTAERYTHRYL PHOSPHONATES AND THEIR USE IN SELF-EXTINGUISHING THERMOPLASTIC POLYMERIC COMPOSITIONS

[75] Inventors: William Giroldini; Gianluigi Landoni; Antonio Rinaldi; Carlo Neri, all of Milan, Italy

[73] Assignee: Enichem Synthesis S.p.A., Palermo, Italy

[21] Appl. No.: 927,212

[22] Filed: Aug. 6, 1992

[30] Foreign Application Priority Data

Aug. 7, 1991 [IT] Italy ........................ MI91 A 002216

[51] Int. Cl.[5] .................. C07F 9/6509; C07F 9/6521; C07F 9/6574

[52] U.S. Cl. .................................... 544/230; 544/195; 556/174; 558/77

[58] Field of Search .................. 558/77; 544/230, 195; 556/174

[56] References Cited

U.S. PATENT DOCUMENTS

| | | | |
|---|---|---|---|
| 4,086,208 | 4/1978 | Murayama et al. | 528/167 |
| 4,174,343 | 11/1979 | Hardy et al. | 524/120 |
| 4,217,267 | 8/1980 | Hoffmann et al. | 524/120 |
| 4,599,375 | 7/1986 | Berté et al. | 524/100 |

FOREIGN PATENT DOCUMENTS 1522081 8/1978 United Kingdom .

OTHER PUBLICATIONS

CIBA, Ltd.; *Chem. Abstr.* 1965, 63(7), 8405h; abstract of FR 1,395,178.

*Primary Examiner*—Mary C. Lee
*Assistant Examiner*—Michael G. Ambrose
*Attorney, Agent, or Firm*—George P. Hoare, Jr.

[57] ABSTRACT

A new group of pentaerythryl diphosphonates and poly(pentaerythryl diphosphonates) are described. Flame-retardant compositions are also described, which include a thermoplastic polymer and a certain amount of self-extinguishing agent consisting of one of the above-mentioned pentaerythryl diphosphonates or poly(pentaerythryl diphosphonates).

5 Claims, No Drawings

PENTAERYTHRYL PHOSPHONATES AND THEIR USE IN SELF-EXTINGUISHING THERMOPLASTIC POLYMERIC COMPOSITIONS

The present invention relates to new pentaerythryl diphosphonates and poly(pentaerythryl diphosphonates).

Moreover, it relates to self-extinguishing thermoplastic polymeric compositions containing a thermoplastic polymer and certain quantities of self-extinguishing agents composed of the above-mentioned pentaerythryl diphosphonates or poly(pentaerythryl diphosphonates).

The production of polymeric compositions having high self-extinguishing values is of considerable importance for security reasons in various fields of application.

Various flame-resistant additives have been proposed in the art for giving flame-resistance to thermoplastic polymers. These are generally composed of metallic compounds, in particular antimony and bismuth oxides and halides, combined with halogenated organic compounds, such as chlorinated paraffins and polybromurated aromatic compounds.

Compositions are obtained which, although being generally satisfactory with respect to their flame-resistant characteristics, have the disadvantage of corrosion in the processing phase and are dangerous during possible combustion due to the emission of smoke containing hydrochloric and hydrobromic acid, and at times also traces of polychloro- or polybromobenzodioxines, substances which are harmful to health even in small concentrations.

Moreover, to obtain high self-extinguishing values (V-O in accordance with the Underwriters Laboratories Test UL94 classification), quantities of additives of about 40% by weight are required, with a consequent increase in the costs of the thermoplastic end product and a considerable decrease in its physical-mechanical characteristics and light stability.

The necessity of using smaller percentages of non-halogenated additives has led to the development of other types of additives, such as those known as "char-forming" which tend to cause the carbonization of the polymer during combustion, with a reduction in obscuring smoke and toxic and corrosive gases. These additives are generally used together with ammonium polyphosphate.

U.S. Pat. No. 4,174,343, for example, describes the use, as flame retardants for olefinic polymers, of mixtures of ammonium polyphosphate and a pentaerythryl diphosphonate having the formula:

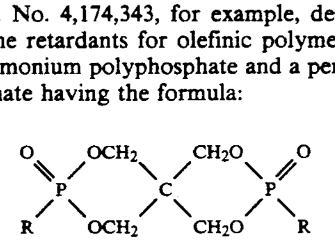

wherein R is methyl, phenyl, benzyl or —CN. The quantities of single components of the mixture used are about 15% by weight, for a total quantity of 30% of additives.

U.S. Pat. No. 4,217,267 describes self-extinguishing compositions including a polyolefinic polymer, a polypentaerythryl diphosphonate having the formula:

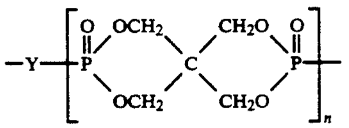

wherein Y is a polyolefinic radical possibly with two aromatic substituents and n is at least 2, and ammonium polyphosphate. Also in this case the quantity of additives is about 30%.

The main disadvantages of these as of other char-forming systems are a still relatively high quantity of additives required, the limited thermal stability under the moulding conditions of the polymer, as well as the appearance of undesired colouring of the end-products.

It is therefore necessary to have flame-resistant additives with improved characteristics compared to those of the known art.

A group of compounds has now been found, which as well as having excellent thermal and colour stability, have unexpectedly high values of the char-forming activity.

These compounds consequently give a satisfactory self-extinguishing effect with a global quantity of additives of 20-23% by weight, thus minimizing the alteration of the physicochemical properties of the polymer and lowering the production costs.

In addition, they can be advantageously used also without other flame-retardant additives, and in particular without ammonium polyphosphate.

The present invention consequently relates to pentaerythryl diphosphonates having the formula:

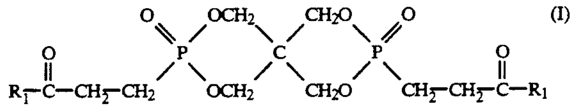

(I)

wherein $R_1$ is OH, OM, $OR_2$ or $NR_3R_4$,

M is Zn, Ca, Mg, Al or Ti, $R_2$ is a linear or branched $C_1$–$C_6$ alkyl, or a linear or branched mono- or poly-hydroxylate $C_2$–$C_6$ alkyl, $R_3$ and $R_4$, the same or different among them, are H, a linear or branched $C_1$–$C_6$ alkyl, a linear or branched amino- or hydroxy-substituted $C_2$–$C_6$ alkyl, a heterocyclic residue, or together form a non aromatic heterocyclic structure on the nitrogen atom, possibly containing one or more further heteroatoms.

The present invention also relates to poly(pentaerythryl diphosphonates) having the formula:

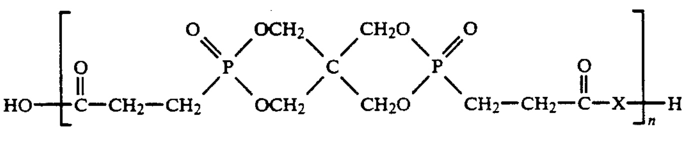

(II)

wherein

X is —O—$R_5$—O— or

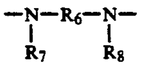

$R_5$ is a linear or branched $C_2$–$C_6$ alkyl, or an aromatic radical, $R_6$ is a linear or branched $C_2$–$C_6$ alkyl, or an aromatic or heterocyclic radical, $R_7$ and $R_8$, the same or different, are H, a linear or branched $C_1$–$C_6$ alkyl, or together a $C_1$–$C_2$ alkylene, n is between 2 and 50.

Another aspect of the present invention relates to self-extinguishing thermoplastic polymeric compositions including a thermoplastic polymer selected from olefinic polymers or copolymers, linear polyesters, unsaturated polyesters, polyurethanes, acrylonitrile-styrene copolymers (SAN) and acrylonitrile-butadiene-styrene terpolymers (ABS), and a quantity of self-extinguishing additive selected from pentaerythryl diphosphonates having formula (I) and poly(pentaerythryl diphosphonates) having formula (II).

In the above polymeric compositions, the additive having formula (I) or formula (II) is present in total quantities of 15 to 35 parts by weight every 100 parts by weight of thermoplastic polymer, and preferably from 15 to 25 parts by weight every 100 parts by weight of thermoplastic polymer.

Optionally, a part of the total quantity of additive required can be substituted by ammonium polyphosphate or a neutral phosphate of an amine having the formula $NHR_3R_4$, wherein $R_3$ and $R_4$ have the above-defined meaning.

The ratio between the additive having formula (I) or (II) and the ammonium polyphosphate or neutral phosphate of the amine can vary from 2:1 to 1:3.

In the compound having formula (I), $R_2$ is preferably a $C_1$–$C_2$ alkyl or a mono- or poly-hydroxylate $C_2$ alkyl; $R_3$ and $R_4$, the same or different, when they are an alkyl are preferably $C_1$–$C_2$, whereas when they are an amino- or hydroxy-substituted alkyl they are preferably $C_2$.

In the compound having formula (II), when $R_5$ is an alkyl, it is preferably $C_2$; when $R_6$ is an alkyl it is preferably $C_2$; when $R_7$ and $R_8$, the same or different, are an alkyl, they are preferably $C_1$–$C_2$.

The particularly preferred additives having formula (I) and formula (II) are those wherein $R_1$ and X respectively represent the piperazine residue. These compounds are characterized by particularly high self-extinguishing values. This is due to the presence of a considerable synergism between the char-forming capacity of the pentaerythrol nucleus and that of the piperazine nucleus.

In the compositions of the present invention it is particularly advantageous to use an additive of the polymeric type having formula (II). In this case, owing to the scarse solubility of these compounds in water and organic solvents compared to compounds of the monomeric type having formula (I), polymeric compositions are obtained, whose self-extinguishing properties are less sensitive to contact with solvents.

With respect to thermoplastic polymers to be made flame-retardant, the preferred olefinic polymers are low, medium and high density polyethylene, polypropylene and polystyrene; preferred linear polyesters are polyethyleneterephthalate and polybutyleneterephthalate.

Particularly preferred are low, medium or high density polyethylene and polypropylene.

The additives of the present invention can be obtained by various methods of synthesis starting from the corresponding phosphite having the formula:

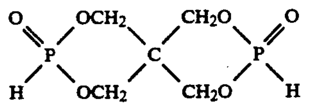

(III)

(C.A.S.=27198-72-7), which can, in turn, be prepared, for example, in accordance with a process described in U.S. Pat. No. 4,070,336.

By reacting the phosphite (III) with acrylic acid, compound (I) is obtained wherein $R_1$ is OH. A bulk reaction is carried out, at a temperature of 120°–135° C., for a period of 2 hours. The product is isolated by filtration after eliminating the excess acrylic acid under vacuum.

By reaction of the above product with an oxide, hydroxide or alcoholate of Zn, Ca, Mg, Al or Ti, at a temperature of 120°–140° C. the salts derived from the acid are obtained, i.e. compounds having formula (I) wherein $R_1$ is OM, M having the above meaning. The reaction can be carried out under vacuum to facilitate the elimination of water or reaction alcohol.

Compounds having formula (I) wherein $R_1$ is $OR_2$, $R_2$ having the above-defined meaning, are obtained by reaction of the phosphite (III) with the corresponding esters of acrylic acid such as methyl acrylate and ethyl acrylate. The reaction is carried out in the presence of solvents such as toluene, dioxane or acetonitrile and an organic base such as triethylamine at a temperature of 120°–145° C. The product is recovered after distillation of the solvent.

When the phosphite (III) is reacted with a diester of acrylic acid, such as bis-acrylate of ethylenic glycol, a product having formula (II) is obtained, wherein X is $OR_5O$, wherein $R_5$ has the above-defined meaning.

Two different methods can be used for the preparation of amides having formula (I) wherein $R_1$ is $NR_3R_4$, $R_3$ and $R_4$ having the above-defined meaning.

The acid having formula (I), wherein $R_1$ is OH, can be reacted with the preselected amine. A salt is obtained which, on heating under vacuum at a temperature of 180°–200° C., eliminates water and produces the corresponding amide.

Alternatively, the phosphite (III) is reacted with the preselected amide of acrylic acid in the presence of a tertiary amine. Examples of suitable amides are acrylamide, N-methyl acrylamide, N,N-dimethylacrylamide, morpholinacrylamide. This latter process is preferable when the amine to be reacted with the acid according to the first process has a low boiling point, and the salt which is formed tends to separate in the constituents before amidation has been completed.

Compounds having formula (II) can also be prepared with both methods, wherein X is $-N(R_7)R_6N(R_8)-$, where $R_6$, $R_7$ and $R_8$ have the meaning defined above. Depending on which method is used, the procedure starts from a di- or polyamine such as piperazine, melamine or ethylendiamine, or from a diamide such as 1,4-diacrylpiperazine or ethylene diaminoacrylamide.

The ammonium polyphosphate used has the formula:

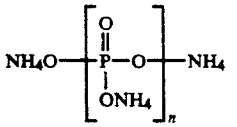

wherein n can vary within the range of 50 to 1000. For example, the commercial products EXOLIT 422 of Hoechst, or PHOS CHECK P-30 of Monsanto can be used.

In the class of neutral amine phosphates having the formula $NHR_3R_4$, melanime phosphate and ethylendiamine are preferred.

The above phosphates can be prepared according to the method described in U.S. Pat. No. 4,599,375.

The self-extinguishing thermoplastic polymeric compositions of the present invention may additionally contain one or more additives selected, for example, from antioxidants, heat and light stabilizers, metal disactivators, basic co-stabilizers and nucleating agents.

The self-extinguishing compositions of thermoplastic polymers according to the present invention can be prepared using any of the known techniques in the art which are suitable for homogenizing the polymer with the additives.

It is common practice to grind the additive or additives to reduce them to powder with a grain size ranging from 1 to 200 microns. The powder thus obtained is mixed with the thermoplastic polymer in pellets, and this mixture is extruded to obtain pellets having the desired self-extinguishing composition.

The following examples provide a better illustration of the present invention but do not limit it in any way.

EXAMPLE 1

Preparation of 3,9-(bis-2,2'-carboxyethyl)-3,9-dioxo-2,4,8,10-tetraoxo-3,9-diphosphaspiro(5,5)undecane acid.

56.4 g (0.247 moles) of the phosphite having formula (III), 39.0 g of acrylic acid, 0.2 g of p-hydroxyanisol and 10 ml of toluene are charged into a 500 ml flask equipped with a stirrer, reflux condenser, and immersed in an oil heating-bath. The mixture is brought to a temperature of 125°-130° C. and kept at this temperature for two hours. When the temperature reaches 100° C., the contents of the flask are in the form of a colourless homogeneous liquid. After a further two hours, when the mass becomes denser, the temperature of the oil bath is raised to 150° C. and a vacuum is applied (25 mm Hg) until all the excess acrylic acid and toluene have been removed by distillation, and the mixture is then left to cool.

About 90 g of a white solid are obtained, which are chopped, washed with toluene, dried under vacuum and then finely ground. The product proves to be soluble in aqueous ammonia and in heated methanol, and insoluble in the common organic solvents. It does not melt nor decompose up to 280° C.

Characterization of the product

Elemental analysis: Carbon 35.5%, hydrogen 4.6%, phosphorous 17.0%.

EXAMPLE 2

Preparation of the aluminium salt of 3,9-(bis-2,2'-carboxyethyl) -3,9-dioxo-2,4,8,10-tetraoxo-3,9-diphosphaspiro (5,5)undecane acid.

56.4 g (0.247 moles) of the phosphite having formula (III), 39.0 g of acrylic acid, 0.2 g of p-hydroxyanisol and 10 ml of xylene are charged into a 500 ml flask equipped with a stirrer, reflux condenser, and immersed in an oil heating-bath. The mixture is brought to a temperature of 130° C. and kept at this temperature for two hours, until the liquid mass becomes quite dense. At this stage a solution of 33.6 g (0.165 moles) of aluminium isopropylate in 60 ml of isopropylic alcohol is slowly added.

Vapours of isopropylic alcohol are released, and a white precipitate is formed. 100 ml of xilene are added, the temperature of the oil bath is raised to 140° C. and a vacuum is slowly applied (20 mm Hg) until all the excess acrylic acid, xilene and isopropylic alcohol has been removed by distillation. The mixture is left to cool, the white product is chopped, finely ground, washed with heated isopropanol, and is then dried under vacuum at 160° C.

96 g of a white powder, insoluble in the common organic solvents, are obtained.

Characterization of the product

Elemental analysis: Carbon 34.6%, hydrogen 4.5%, phosphorous 15.7%, aluminium 4.9%.

EXAMPLE 3

Preparation of 3,9-(bis-2,2'-ethylcarboxyethyl)-3,9-dioxo-2,4,8,10-tetraoxo-3,9-diphosphaspiro(5,5)undecane ester.

115.0 g (0.5 moles) of the phosphite having formula (III), 100.0 g (1 mole) of ethyl acrylate, 50 ml of dioxane, 50 ml of triethylamine and 0.3 g of p-hydroxyanisol antioxidant are charged into a 700 ml autoclave. The mixture is brought to a temperature of 130° C. and kept at this temperature for five hours. The heating is then stopped and the mixture is left to cool. 50 ml of acetone are added, the precipitate is filtered, washed with a small amount of acetone and toluene and finally dried.

130 g of a white powder are obtained, which proves to be soluble in methyl alcohol, acetone, heated toluene and water. The product melts at 136° C.

Characterization of the product

Elemental analysis: Carbon 42.6%, hydrogen 6.0%, phosphorous 14.9%.

EXAMPLE 4

Preparation of the bis-amide of3,9-(bis-2,2'-carboxyethyl)-3,9-dioxo-2,4,8,10-tetraoxo-3,9-diphosphaspiro(5,5)undecane acid with melamine.

A mixture in powder of 38.0 g (0.1 moles) of 3,9-(bis-2,2'-carboxyethyl)-3,9-doxa-2,4,8,10-tetraoxo-3,9-diphosphaspiro (5,5)undecane acid and 25.5 g (0.2 moles) of melamine is charged into a 500 ml flask equipped with a stirrer and immersed in an oil heating-bath. The mixture is progressively heated under stirring (20 mm Hg) up to a temperature of 190° C. The mass is kept under these conditions for six hours. The heating is then stopped and the mixture left to cool. The product is chopped, finely ground, washed with water and acetone, and finally dried at 150° C. and 20 mm Hg.

60 g of a pale yellow product are obtained, which proves to be insoluble in all solvents and thermally stable up to 280° C.

Characterization of the product

Elemental analysis: Carbon 34.3%, hydrogen 4.9%, phosphorous 10.6%, nitrogen 29.0%.

EXAMPLE 5

Preparation of the polyamine of 3,9-(bis-2,2'-carboxyethyl)-3,9-dioxo-2,4,8,10-tetraoxo-3,9-diphosphaspiro(5,5)undecane acid with piperazine.

46.0 g(0.2 moles) of phosphite (III), 39.0 g of 1,4-diacrylpiperazine prepared according to the process described in "La chimica e l'industria", Vol. 49, pages 271–278, 6 ml of tributylamine and 40 ml of diethyldiethylenether are charged into a 500 ml flask equipped with a stirrer and immersed in an oil heating-bath. The mixture is brought to 130° C. and kept at this temperature for two hours, then to 160° C. for a further two hours.

The heating is then stopped and the mixture is left to cool. The product is filtered, washed with water and acetone, dried under vacuum (5 mm Hg) at 180 and, in the end, finely ground.

80 g of a yellowish-white product are obtained, which proves to be insoluble in all organic solvents and thermally stable up to at least 280° C.

Characterization of the product

Elemental analysis: Carbon 42.2%, hydrogen 6.0%, phosphorous 14.2%, nitrogen 6.9%.

EXAMPLE 6

Preparation of the bis-amide of 3,9-(bis-2,2'-carboxyethyl-3,9-dioxa-2,4,8,10-tetraoxa-3,9-diphosphaspiro(5,5)undecane acid with diethanolamine.

57.0 g (0.25 moles) of phosphite (III), 39.0 g (0.53 moles) of acrylic acid, 0.2 g of p-hydroxyanisol and 10 ml of toluene are charged into a 500 ml flask equipped with a stirrer and immersed in an oil heating-bath. The mixture is brought to 125°–130° C. and kept at this temperature for two hours. When the reaction mass becomes extremely dense, a solution of 55 g (0.52 moles) of diethanolamine in 60 ml of isopropanol is added. The solvent is removed by distillation. The reaction mass is progressively heated under vacuum (20 mm Hg) up to a temperature of 190° C. and kept under these conditions for three hours. The pressure is further lowered to 5 mm Hg and the mass is kept under these conditions and at the same temperature for a further four hours. The heating is then stopped and the mixture is left to cool. The product is chopped, finely ground, washed with water and acetone, and finally dried under vacuum (20 mm Hg) at 160° C.

130 g of a yellowish product are obtained, which proves to be insoluble in all organic solvents and thermally stable up to at least 280° C.

Characterization of the product

Elemental analysis: Carbon 42.1%, hydrogen 6.6%, phosphorous 11.3%, nitrogen 5.5%.

EXAMPLE 7

Preparation of the polyester of 3,9-(bis-2,2'-carboxyethyl)-3,9-dioxa-2,4,8,10-tetraoxa-3,9-diphosphaspiro(5,5)undecane acid with ethylene glycol.

57.0 g (0.25 moles) of phosphite (III), 20 ml of diethyldiethylenether, 6 ml of tributylamine and 44.5 g (0.26 moles) of diacrylester of ethylene glycol are charged into a 500 ml flask equipped with a stirrer and immersed in an oil heating-bath. The mixture is brought to a temperature of 130° C. and kept at this temperature for an hour. The reaction mass is then progressively heated under vacuum (20 mm Hg) to a temperature of 190° C. and kept under these conditions for three hours. The heating is then stopped and the mixture is left to cool. The product is chopped, finely ground, washed with water and acetone, and finally dried under vacuum (20 mm Hg) at 150° C.

101 g of a slightly yellowish product are obtained, which proves to be insoluble in all organic solvents and thermally stable up to at least 260° C.

Characterization of the product

Elemental analysis: Carbon 41.0%, hydrogen 5.5%, phosphorous 15.0%.

EXAMPLES 8-16

Formulations of polypropylene with flame-resistant additives

To evaluate the self-extinguishing capacity of the compositions of the present invention several formulations of polypropylene with different additives were prepared.

These formulations were extruded in a 30 mm single-screw extruder, with a temperature profile increasing from 190° to 220° C., and transformed into granules. The granules were then moulded into slabs having a thickness of ⅛ inch (3 mm), from which test samples were taken according to the requirements of the flammability test ASTM D-2863-77 and Underwriters Laboratories Test UL94, Vertical Test Method (3.10–3.15, September 1973).

In the first test the flammability of a polymeric material was determined in relation to the volumetric concentration of oxygen. This relation is expressed in L.O.I., i.e. as a minimum percentage of oxygen capable of maintaining the combustion of the test sample in an oxygen-nitrogen atmosphere which immerses the test sample in an upward flow (good self-extinguishing values correspond to high L.O.I. values).

In the second test the behaviour of the test samples to fire is evaluated. The test samples are classified in decreasing order of self-extinguishing properties according to the scale V-0, V-1, V-2.

The compositions of the test samples and results of the test are summarized in Table I.

TABLE I

| Example | Additive | % P.P. | % A.P. | % ANOX 20 | L.O.I. | UL94 |
|---|---|---|---|---|---|---|
| 8 | Ex. 1 10% | 75 | 14 | 1 | 32 | V0 |
| 9 | Ex. 2 10% | 75 | 14 | 1 | 28 | V0 |
| 10 | Ex. 4 10% | 75 | 14 | 1 | 31 | V2 |
| 11 | Ex. 5 10% | 75 | 14 | 1 | 36 | V0 |
| 12 | Ex. 6 10% | 75 | 14 | 1 | 28 | V0 |
| 13 | Ex. 7 10% | 75 | 14 | 1 | 29 | V0 |

TABLE I-continued

| Example | Additive | % P.P. | % A.P. | % ANOX 20 | L.O.I. | UL94 |
|---|---|---|---|---|---|---|
| 14 | Ex. 4 25% | 74 | — | 1 | 27 | — |
| 15 | Ex. 5 25% | 74 | — | 1 | 29 | V0 |
| 16 | Ex. 6 25% | 74 | — | 1 | 26 | — |

P.P. = polypropylene
A.P. = ammonium polyphosphate
ANOX 20 = tetrakis[3-(3,5-di-t-buthyl-4-hydroxyphenyl)propionyloxymethane - Trade name of Enichem Synthesis.

We claim:

1. A pentaerythryl diphosphonate having the formula:

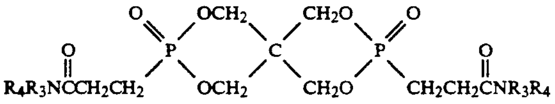

wherein:

$R_3$ and $R_4$ are the same or different and are linear or branched $C_1$–$C_6$ alkyl, linear or branched amino- or hydroxy-substituted $C_2$–$C_6$ alkyl, a melamine residue, or together with the N to which they are attached form a non-aromatic heterocyclic radical optionally having one or more additional heteroatoms.

2. A pentaerythryl diphosphonate according to claim 1, wherein $—NR_3R_4$ represents a piperazine residue.

3. A poly(pentaerythryl diphosphonate) having the formula:

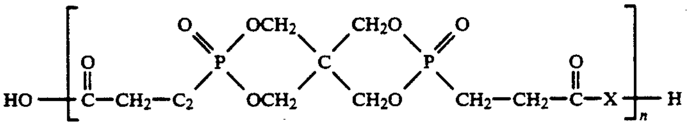

wherein

X is

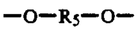 or 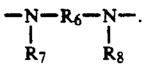

$R_5$ is a linear or branched $C_2$–$C_6$ alkyl, or an aromatic radical, $R_6$ is a linear or branched $C_2$–$C_6$ alkyl, or a $C_6$ aromatic radical or a melamine radical, $R_7$ and $R_8$, the same or different, are H, a linear or branched $C_1$–$C_6$ alkyl, or together a $C_1$–$C_2$ alkylene, n is between 2 and 50.

4. A poly(pentaerythryldiphosponates) according to claim 3, wherein $R_5$ and $R_6$ are a $C_2$ alkyl, and $R_7$ and $R_8$, the same or different, are a $C_1$–$C_2$ alkyl.

5. A poly(pentaerythryldiphosphonates) according to claim 3, wherein X represents the piperazine residue.

* * * * *